(12) United States Patent
Baker et al.

(10) Patent No.: US 6,420,361 B1
(45) Date of Patent: Jul. 16, 2002

(54) SOIL PESTICIDE

(76) Inventors: George B. Baker, 30301 Riverview, Junction City, OR (US) 97448; Jimmie D. Petty, 3400 Winners Cir., Columbia, MO (US) 65202; Richard M. Schwarz, 3806 NorthrideTer., St. Joseph, MO (US) 64506

( * ) Notice: Subject to any disclaimer, the term of this patent is extended or adjusted under 35 U.S.C. 154(b) by 0 days.

(21) Appl. No.: 09/663,039

(22) Filed: Sep. 15, 2000

Related U.S. Application Data

(60) Provisional application No. 60/157,123, filed on Oct. 4, 1999.

(51) Int. Cl.[7] ............... A61K 31/54; A01N 25/00
(52) U.S. Cl. ................... 514/223.8; 504/405
(58) Field of Search ............ 514/223.8; 424/405

(56) References Cited

U.S. PATENT DOCUMENTS

| | | |
|---|---|---|
| 3,113,908 A | 12/1963 | Pieroh et al. |
| 3,205,129 A | 9/1965 | Kenaga |
| 3,240,666 A | 3/1966 | Kufsaras |
| 4,994,487 A | 2/1991 | Haglund |

FOREIGN PATENT DOCUMENTS

| | | | |
|---|---|---|---|
| JP | 07215809 | * | 8/1995 |

OTHER PUBLICATIONS

Whitehead et al, Control of potato cyst–nematode, Globodera pallida, on tomatoes grown under glass, by applying steam or chemical nematicides to the soil, Ann. Appl. biol., vol. 92 (2), pp. 275–278, 1979.*

Whitehead et al, Control of potato cyst–nematode, Heterodera rostochiensis, in sandy, peaty, and silt loam soils by dazomet and telone applied in different ways, 1973.*

Baines et al, "Nematocidol and Fungirdol Properties of Some Soil Fumigants", Phytopathology, Jun. 1966, pp. 691–698, vol. 56, No. 6.

Telore —Speciman Label —original date unknown but attached copy bears a fax dale of Sep. 28, 1998.

Dazomet —label —original date unknow but attached copy bears a date of (fax) of Sep. 28, 1998.

* cited by examiner

Primary Examiner—Alton Pryor
(74) Attorney, Agent, or Firm—Robert E. Howard

(57) ABSTRACT

A liquid soil pesticide composition containing tetrahydro-3,5-dimethyl-2H-1,3,5-thiadiazine-2-thione. The composition contains 1,3-dichloropropene as a first co-solvent and a second co-solvent selected from the group consisting of dimethyl sulfoxide and dimethylformamide.

11 Claims, No Drawings

SOIL PESTICIDE

CROSS-REFERENCE TO RELATED APPLICATIONS

This application claims the benefit of U.S. Provisional Application No. 60/157,123, filed Oct. 4, 1999.

BACKGROUND OF THE INVENTION

This invention relates to a soil pesticide composition. More particularly the invention relates to a liquid composition useful as a nematocide.

Many compounds have been used as nematocides for cropland soils. It is preferred to use compounds that can be applied as liquid solutions that can soak into soils as opposed to application of dry compositions which can be blown away by the wind.

One such compound is tetrahydro-3,5-dimethyl-2H-1,3,5-thiadiazine-2-thione (hereinafter referred to as TDTT), sold under the trademark "Dazomet" by Verichem Inc. TDTT is not very soluble or stable in commonly used agricultural solvents or carriers, and is typically applied in granular form. Where it is applied as a liquid formulation its concentration is limited to less than 15% by weight.

It would be very useful to be able to deliver TDTT to the soil as a stable solution and in concentrations greater than 15% by weight.

SUMMARY OF THE INVENTION

It is an object of this invention to provide a composition of TDTT in an environmentally acceptable solvent at concentrations greater than about 15% by weight for use as a soil pesticide, and particularly as a nematocide.

The pesticide composition of the present invention is comprised of TDTT, a first co-solvent of 1,3-dichloropropene (1,3-D), and a second co-solvent that is an aprotic polar organic solvent, such as dimethyl sulfoxide (DMSO) or dimethylformamide (DMF), where the TDTT is present in an amount greater than about 15% by weight of the composition.

DESCRIPTION OF PREFERRED EMBODIMENTS

The pesticidal composition of the present invention comprises between about 15% and about 35% by weight TDTT, between about 25% and about 45% by weight 1,3-D as a first co-solvent, and between about 25% and about 50% by weight of an aprotic polar organic solvent as a second co-solvent, the second co-solvent preferably being selected from the group consisting of DMSO and DMF.

Small amounts of surfactants, up to about 5% by weight of the composition, may be used to maintain TDTT solubility over a wide range of temperatures. Suitable surfactants include, but are not limited to, polyethylene glycols or tergitols.

One of the surprising benefits of this invention is in discovering that 1,3-D acts as a solvent for TDTT. 1,3-D, which is sold under the trademark "Telone" by DowElanco is itself a known pesticide, although at the concentrations employed in the composition of the present invention, i.e., at an effective application level of less than about 15 gallons per acre, it would not by itself exhibit pesticidal activity.

The liquid pesticide compositions of this invention are applied to the soil to be treated at a rate effective to control pest infestation, preferably at a rate of about 10 to about 20 gallons per acre.

The following examples illustrate the use of the composition of the invention as a nematocide. However, the composition may be used to control other soil pests.

EXAMPLE 1

Preparation of the Pesticide Composition of the Invention

A composition containing 10.2 grams of TDTT, 15.98 grams of 1,3-D, and 17.6 grams of DMSO was prepared as follows:

Into a 100 ml. beaker equipped with a magnetic stirrer was placed 10.2 grams of TDTT and 14.1 grams of DMSO. The mixture was stirred for 10 minutes, during which time some of the TDTT dissolved. Then 15.98 grams of 1,3-D was added and stirring continued for an additional 10 minutes. Most of the TDTT dissolved, and complete solution was obtained upon addition of 3.5 grams of DMSO. The TDTT remained in solution at room temperature.

EXAMPLE 2

Evaluation as a Nematocide

A sandy loam soil (85% sand, 10% silt, 5% clay, and 0.5% other material) was infested with a mixture of eggs and juveniles of the Columbia root-knot nematode, *Meloidogyne chitwoodi*. Five hundred gram samples of infested soil were treated at the rates of 10, 15, and 20 gallons per acre with the composition of Example 1. Untreated soil served as a control. After treatment the soil was placed in plastic bags and sealed in a mason jar. The jars were incubated at room temperature for one week before they were placed in clay pots. The pots were maintained moist for two weeks on a greenhouse bench to allow the soil to aerate and the fumigant to dissipate. Three week old Rutgers tomato seedlings were planted in each pot to determine the presence of live nematodes in the treated soil. This tomato cultivar is an excellent host for *M. chitwoodi* and nematodes that have survived treatment will penetrate and develop in the root system. Two weeks after planting the tomato roots were washed free from soil, stained with acid fuchsin, and the number of infective nematodes were determined. The results were:

| Treatment | Gallons/acre | Number of M. chitwood/pot* |
|---|---|---|
| Untreated | — | 387 ± 93 |
| Treated | 10 | 0 ± 0 |
| " | 15 | 0 ± 0 |
| " | 20 | 0 ± 0 |

*± statistical error; average of five replicates

The results show that the composition of Example 1 was effective in eliminating *M. chitwoodi* from the infested soil. No nematodes were detected in tomato roots planted in the treated soil. The two week waiting period before planting was sufficient for the composition of Example 1 to dissipate; no phytotoxicity was observed on the tomato seedlings.

EXAMPLE 3

A composition containing 10.1 grams of TDTT, 19.7 grams of 1,3-D, and 18.1 grams of dimethylformamide was prepared as described in Example 1. The testing procedure described in Example 2 was repeated for this composition. The results were the same, i.e., no nematodes were detected in soil treated with this composition at any of the three rates of application.

It will be obvious to those having skill in the art that many changes may be made to the details of the above-described embodiments of this invention without departing from the underlying principles thereof. The scope of the present invention should, therefore, be determined only by the following claims.

The invention claimed is:

1. A liquid pesticide composition for applying to soil comprising: about 15% to about 35% by weight tetrahydro-3,5-dimethyl-2H-1,3,5-thiadiazine-2-thione, about 25% to about 45% by weight of 1,3-dichloropropene as a first co-solvent, and about 25% to about 50% by weight of an aprotic polar organic solvent selected from the group consisting of dimethyl sulfoxide and dimethylformamide as second co-solvent wherein the liquid is a solution.

2. The composition of claim 1 additionally containing up to about 5% by weight of a surfactant.

3. A process of controlling infestations of pests in soil comprising applying a liquid composition comprising about 15% to about 35% by weight tetrahydro-3,5-dimethyl-2H-1,3,5-thiadiazine-2-thione, about 25% to about 45% by weight of 1,3-dichloropropene as a first co-solvent, and about 25% to about 50% by weight of an aprotic polar organic solvent selected from the group consisting of dimethyl sulfoxide and dimethylformamide as second co-solvent to the soil at a rate effective to control said pest infestation wherein the liquid is a solution.

4. The process of claim 3 wherein said liquid composition additionally contains up to about 5% by weight of a surfactant.

5. The process of claim 3 wherein said pests are nematodes.

6. The process of claim 3 in which said liquid composition is applied to the soil at the rate of about 10 to about 20 gallons per acre.

7. The process of claim 4 in which said liquid composition is applied to the soil at the rate of about 10 to about 20 gallons per acre.

8. The process of claim 3 in which said pests are nematodes.

9. A liquid pesticide composition adapted to be applied to soil at an effective rate of about 10 to about 20 gallons per acre comprising: about 15% to about 35% by weight tetrahydro-3,5-dimethyl-2H-1,3,5-thiadiazine-2-thione, about 25% to about 45% by weight of 1,3-dichloropropene as a first co-solvent, about 25% to about 50% by weight of an aprotic polar organic solvent selected from the group consisting of dimethyl sulfoxide and dimethylformamide as a second co-solvent, and up to about 5% by weight of a surfactant wherein the liquid is a solution.

10. A process of controlling infestations of pests in soil comprising applying a liquid composition comprising about 15% to about 35% by weight tetrahydro-3,5-dimethyl-2H-1,3,5-thiadiazine-2-thione, about 25% to about 45% by weight of 1,3-dichloropropene as a first co-solvent, about 25% to about 50% by weight of an aprotic polar organic solvent selected from the group consisting of dimethyl sulfoxide and dimethylformamide as a second co-solvent, and up to about 5% by weight of a surfactant to the soil at the rate of about 10 to about 20 gallons per acre wherein the liquid is a solution.

11. The process of claim 10 in which said pests are nematodes.

* * * * *